(12) United States Patent
Saumureau

(10) Patent No.: US 10,561,902 B2
(45) Date of Patent: Feb. 18, 2020

(54) GOGGLES

(71) Applicant: DECATHLON, Villeneuve d'Ascq (FR)

(72) Inventor: Damien Saumureau, Saint Pee sur Nivelle (FR)

( * ) Notice: Subject to any disclaimer, the term of this patent is extended or adjusted under 35 U.S.C. 154(b) by 227 days.

(21) Appl. No.: 15/538,151

(22) PCT Filed: Dec. 15, 2015

(86) PCT No.: PCT/FR2015/053521
§ 371 (c)(1),
(2) Date: Jun. 20, 2017

(87) PCT Pub. No.: WO2016/102815
PCT Pub. Date: Jun. 30, 2016

(65) Prior Publication Data
US 2017/0368416 A1 Dec. 28, 2017

(30) Foreign Application Priority Data
Dec. 22, 2014 (FR) ...................................... 14 63164

(51) Int. Cl.
*A63B 33/00* (2006.01)
*A61F 9/02* (2006.01)

(52) U.S. Cl.
CPC ............ *A63B 33/002* (2013.01); *A61F 9/025* (2013.01); *A63B 2033/004* (2013.01)

(58) Field of Classification Search
CPC .. A63B 33/002; A63B 2033/004; A61F 9/025
(Continued)

(56) References Cited

U.S. PATENT DOCUMENTS 1,846,679 A * 2/1932 Fischer .................. A61F 9/025
2/440
1,923,567 A * 8/1933 Baker ...................... G02C 7/02
351/57
(Continued)

FOREIGN PATENT DOCUMENTS

EP 0525238 A1 2/1993
EP 2452724 A1 5/2012
WO WO-2013094288 A1 6/2013

OTHER PUBLICATIONS

English Translation of International Search Report for International Application No. PCT/FR2015/053521, dated Feb. 22, 2016.

*Primary Examiner* — Katherine M Moran
(74) *Attorney, Agent, or Firm* — Marshall, Gerstein & Borun LLP

(57) ABSTRACT

The invention relates to a pair of googles which comprise a frame with two rims in which an optical unit is respectively intended for being assembled via a reversible attachment device in order to provide an inner attachment of said optical unit in said rim, each device comprising a button and a cavity rigidly connected to an outer edge of the optical unit and the rim, respectively, said button being capable of being inserted into said cavity in order to provide external locking of the optical unit in the rim, each rim having one recess opening onto the rear, each optical unit having a front bearing surface which, in the assembled state, is arranged against a rear complementary bearing surface of said recess, at least one of the outer edges being reversibly deformable to allow the placement and the withdrawal of said button in said cavity when the bearing surfaces are arranged against one another.

16 Claims, 5 Drawing Sheets

(58) Field of Classification Search
USPC .............................................................. 2/426
See application file for complete search history.

(56) References Cited

U.S. PATENT DOCUMENTS

| | | | |
|---|---|---|---|
| 6,749,299 B1 | 6/2004 | Hsu | |
| 7,100,215 B2* | 9/2006 | Shiue | A61F 9/025 2/443 |
| 7,631,400 B2* | 12/2009 | Chiang | A63B 33/002 2/426 |
| 2008/0189837 A1* | 8/2008 | Chiang | A63B 33/002 2/431 |
| 2009/0296042 A1 | 12/2009 | Yeh | |
| 2009/0313746 A1 | 12/2009 | Wang | |
| 2010/0064422 A1 | 3/2010 | Dichiara | |
| 2011/0258761 A1* | 10/2011 | Chou | A63B 33/002 2/445 |

* cited by examiner

GOGGLES

The present application is the US national phase of International Application No. PCT/FR2015/053521, filed Dec. 15, 2015, which claims priority to French Application No. 1463164, filed Dec. 22, 2014. The priority applications are PCT/FR2015/053521 and FR-1463164, are hereby incorporated by reference.

FIELD OF THE DISCLOSURE

The invention relates to a pair of goggles, typically comprising a frame provided with a device for maintaining said goggles on the head of a wearer.

BACKGROUND

Conventionally, the frame has two rims connected by a nose bridge, and in each one of which is assembled an optical unit that comprises a transparent wall through which the vision is carried out.

In certain versions, the optical units are reversibly assembled in the rims, in particular for the purposes of being replaced for example according to the sight of the wearer, of the use and/or of the wear of said unit.

Document EP-2 452 724 proposes goggles in which the reversible attachment is carried out by geometrical means comprising internal and external tabs, with the internal tab being inserted during the assembly into a notch that has a portion protruding towards the inside of the rim.

This realisation allows for an easy assembly of optical units in the rims while still providing a reliable attachment, in particular relatively to the deformation stresses that the frame is subjected to during the use of the goggles.

However, the withdrawal of optical units is difficult to carry out, in particular by requiring manual actuation of the protruding portion which is located on the nose bridge of the frame.

Document WO-2013/094288 propose goggles of which each rim can be provided with an auxiliary optical unit, in particular a solar protection unit, said auxiliary optical unit being positioned in said rim facing a main optical unit by being mounted in an inner peripheral groove formed on the front edge of said rim.

However, this solution does not provide entire satisfaction, in that it forces the wearer to engage the auxiliary optical unit by the front of the rim, which forms an ergonomics that is hardly satisfying. Moreover, the withdrawal of the optical unit is also difficult to carry out.

The invention aims to improve prior art by proposing in particular goggles in which the optical units are assembled simply in the rims by providing a reliable attachment, and this while being easy to actuate manually for the purpose of withdrawing them.

To this effect, the invention proposes a pair of goggles comprising a frame provided with a device for maintaining said goggles on the head of a wearer, said frame having two rims in which an optical unit is respectively intended for being assembled via a reversible attachment device, with each one of said devices comprising complementary geometrical means provided on an inner edge of respectively the rim and the optical unit, said means comprising a protrusion and a groove wherein said protrusion is able to be mounted in order to provide an inner attachment of said optical unit in said rim, with each one of said reversible attachment devices comprising a button rigidly connected to an outer edge of one among the optical unit and the rim and a cavity rigidly connected to an outer edge of the other among the optical unit and the rim, said button being capable of being inserted into said cavity in order to provide external locking of the optical unit in the rim, each rim having one recess opening onto the rear, each optical unit having a front bearing which, in the assembled state, is arranged against a rear complementary bearing surface of said recess, at least one of the outer edges being reversibly deformable to allow the placement and the withdrawal of said button in said cavity when the bearing surfaces are arranged against one another.

BRIEF DESCRIPTION OF THE SEVERAL VIEWS OF THE DRAWINGS

Other particularities and advantages of the invention shall appear in the description which follows, given in reference to the annexed figures, in which.

Figure 1A:
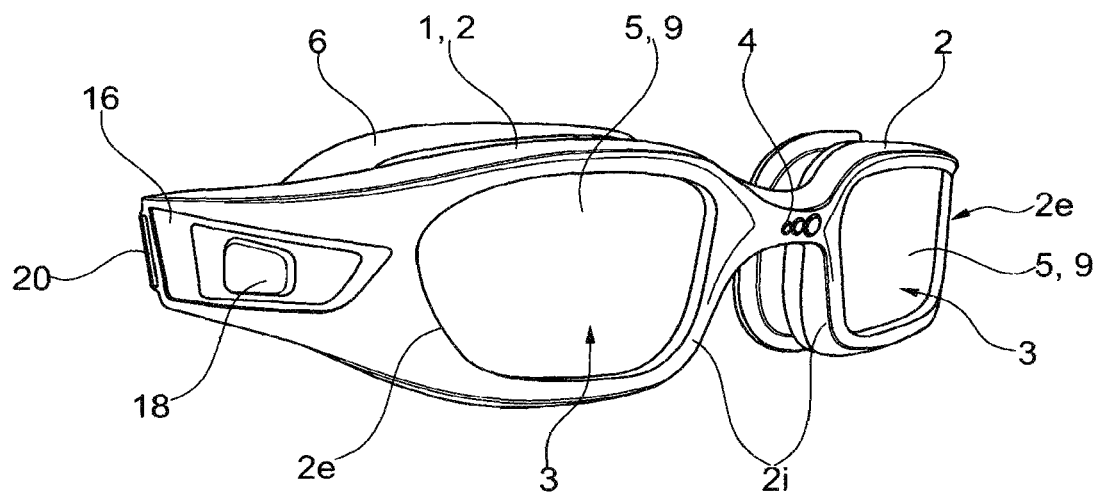
FIG. 1a partially shows goggles according to a first embodiment of the invention, in perspective.

In this description, the terms of positioning in the space are taken in reference to the position of the goggles in relation to the face of a wearer having put on said goggles. In particular, the term "rear" relates to an arrangement facing the face and the term "front" relates to an arrangement opposite the face. Moreover, the terms "inner" and "outer" relate to arrangements respectively close to and far from the nose of the wearer.

In relation with these figures, a pair of goggles is described hereinbelow, in particular intended for the practice of an aquatic activity such as swimming according to FIGS. 1 to 3, or for leisure use or for daily use for sight according to FIG. 4.

The goggles include a frame 1 that has two rims 2 in which an optical unit 3 is respectively intended for being reversibly assembled, as well as a nose bridge 4 that connects the inner edges 2i of each one of said rims and which is intended to be arranged above the nose of a wearer when the latter is wearing said goggles.

The rims 2 and the optical units 3 can be made from a rigid material, for example with a thermoplastic polymer base, in order to allow for their resistance and their reversible assembly by the wearer. Moreover, the nose bridge 4 can be made from a flexible material, for example with an elastomeric polymer base, said nose bridge being able to be overmoulded between the rims 2 in order to connect the inner edges 2i into one part.

In particular, the nose bridge 4 is arranged to hug the shape of the nose of the wearer well and to limit the risks of injury and/or of unsightly markings on the skin of said wearer when the goggles are worn for a long time, with the deformability of said nose bridge also allowing for a good adaptation of the goggles to the morphology of the face of said wearer.

Each optical unit 3 comprises a transparent wall 5 that the wearer inserts into a rim 2 in order to assemble said optical unit to the goggles. The transparent wall 5 is arranged so that the vision is carried out through it when the goggles are worn by the wearer, for example by being of a base of glass or of a transparent thermoplastic polymer material. In particular, optical properties of the transparent wall 5 can be arranged to adapt to the sight of the wearer so that the wearer can select optical units 3 that are suitable for him before assembling them in the rims 2 of his goggles.

Each rim 2 has a recess 7 opening onto the rear and at the centre of which is formed an opening 8. Moreover, the front surface 9 of each transparent wall 5 is arranged in the opening 8 in order to allow for the vision of the wearer, said front surface being surrounded by a front bearing surface 10, which, in the assembled state, is arranged as a front bearing against a complementary bearing surface 11 of the recess 7.

In particular, each optical unit 3 is intended to be assembled in a rim 2 via a reversible attachment device, said attachment providing, in the case of swimming goggles, in particular the seal of the bearing between the bearing surfaces 10, 11 in order to prevent water from penetrating inside the optical unit 3.

Each one of the devices comprises complementary geometrical means provided on an inner edge 2i, 3i of respectively the rim 2 and the optical unit 3. In the figures, the complementary geometrical means include a protrusion 12 and a groove 13 wherein said protrusion is able to be mounted in order to provide an inner attachment of an optical unit 3 in a rim 2.

Figure 2A:
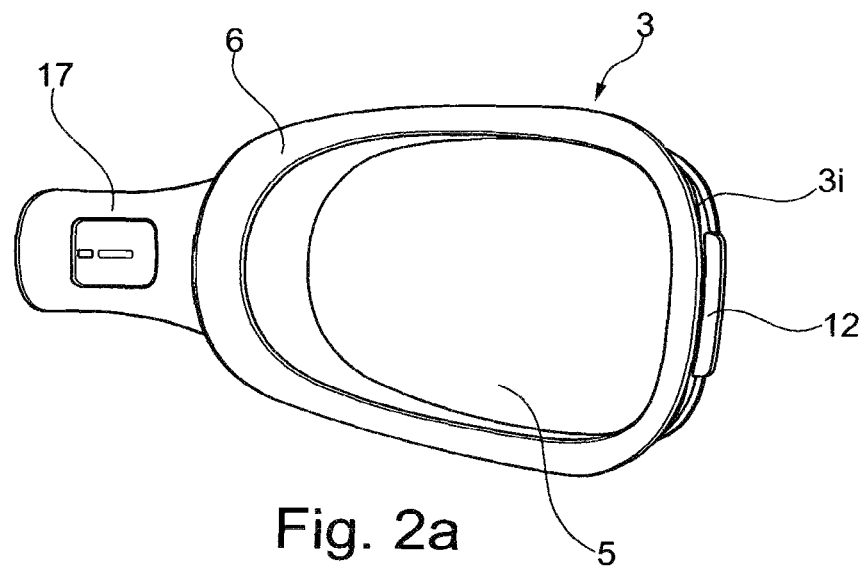
FIG. 2a partially shows an optical unit of the goggles according to FIGS. 1a to 1c, as a rear view.
Figure 2B:
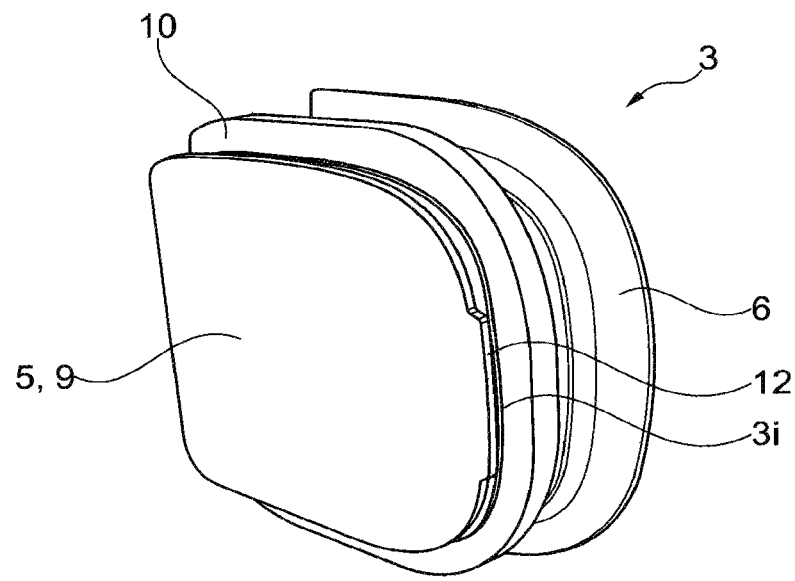
FIG. 2b partially shows an optical unit of the goggles according to FIGS. 1a to 1c, as an inner side view.
Figure 3A:
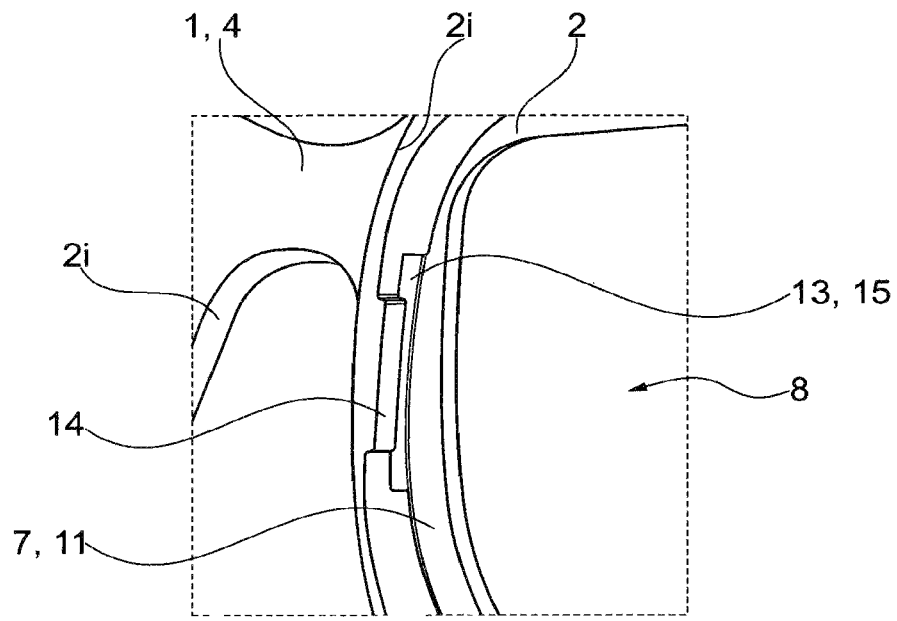
FIG. 3a partially shows a rim of the goggles according to FIGS. 1a to 1c, as a rear view oriented inwards (FIG. 3a)
Figure 4A:
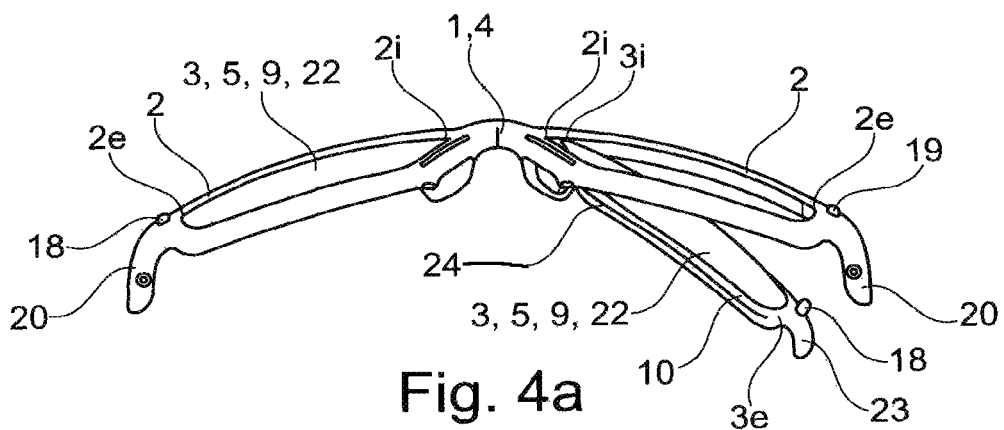
FIG. 4a partially shows goggles according to a second embodiment of the invention, showing in particular the assembly of an optical unit in a rim, as a bottom view.
Figure 4B:
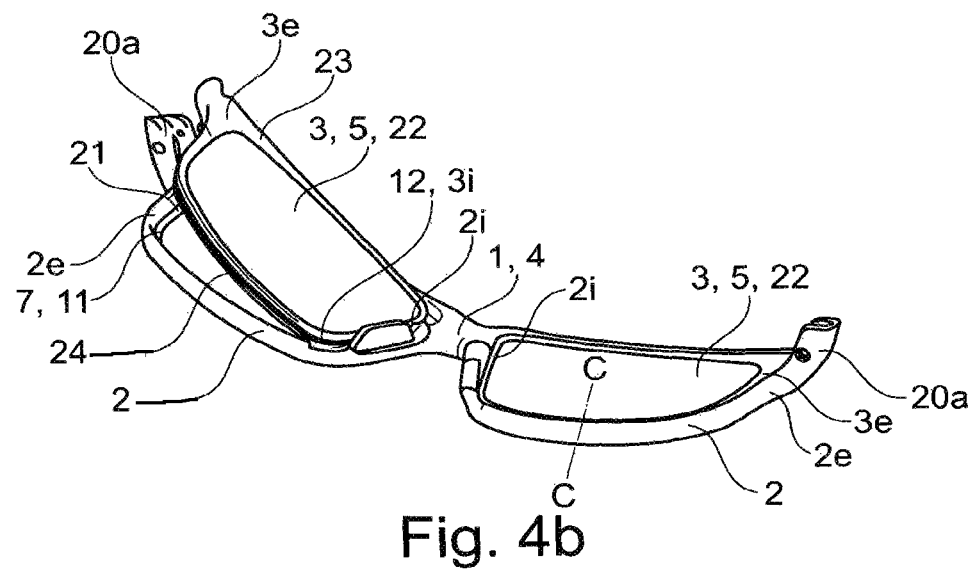
FIG. 4b partially shows goggles according to a second embodiment of the invention, showing in particular the assembly of an optical unit in a rim, in perspective.
Figure 4C:
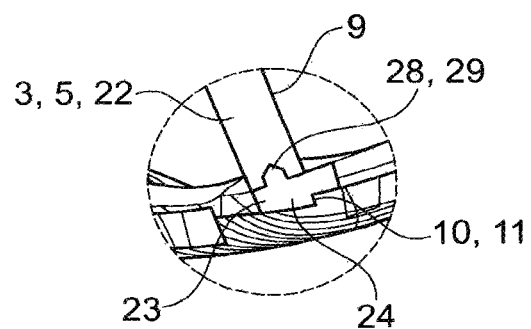
FIG. 4c shows a cross-section according to the line C-C of FIG. 4b of an enlargement of the assembly of the optical unit in the rim.

In relation with FIGS. 2b and 3a, each optical unit 3 has a protrusion 12 that extends interiorly from the inner edge 3i of the transparent wall 5 by being arranged facing towards the front of the bearing surface 10. Alternatively, the protrusion 12 can be formed directly by the inner edge 3i which is then arranged to be able to engage in the groove 13.

Each rim 2 comprises a groove 13 that is formed between the complementary bearing surface 11 and a rear protrusion 14 formed on the recess 7. As such, a groove 13 is formed between a complementary bearing surface 11 and a rear protrusion 14 formed inside a rim 2, in order to allow for a good positioning of the inner attachment. Moreover, each groove 13 has a hole 15 formed in the recess 7 in order to facilitate the insertion of the protrusion 12 in the groove 13.

In order to allow for the withdrawal of the optical units 3, in particular to replace said optical units according to their use and/or their wear, each reversible attachment device further comprises a button 18 rigidly connected to an outer edge 2e, 3e of one among the optical unit 3 and the rim 2 and a cavity 19 rigidly connected to an outer edge 2e, 3e of the other among the optical unit 3 and the rim 2, said button being capable of being inserted into said cavity in order to provide external locking of the optical unit 3 in the rim 2, at least one of the outer edges 2e, 3e being reversibly deformable to allow the placement and the withdrawal of said button in said cavity when the bearing surfaces 10, 11 are arranged against one another.

The fact that the means for locking/unlocking optical units 3 are located on the side of the outer edges 2e, 3e makes it possible to facilitate access to said means, and therefore the manual actuating of said means for the purpose of the withdrawal of the optical units 3. Moreover, the engagement through the rear of the optical units 3 in the rims 2 procures an ergonomics of displacement and of deformation which is satisfactory for locking as well as unlocking.

In the embodiments shown, the outer edge 2e of each rim 2 extends laterally from the complementary bearing surface 11 and comprises a free end provided with a means 20, 20a in order to allow for the attaching of a device for maintaining goggles on the head of the wearer.

In figures, the cavity 19 is formed in the outer edge 2e of the rim 2. Moreover, the button 18 extends over the front of the outer edge 3e of the optical unit 3 and is arranged in such a way as to be able to be withdrawn from the cavity 19 through a manual pressing thereon.

In order to assemble an optical unit 3 in a rim 2, the wearer first mounts the protrusion 12 in the groove 13, in particular by tilting the inner edge 3i of the optical unit 3 towards the inner edge 2i of the rim 2, so as to provide the inner attachment of said optical unit.

Then, the wearer disposes the button 18 in the cavity 19, in particular by folding back the outer edge 3e of the optical unit 3 towards the outer edge 2e of the rim 2 in order to displace the bearing surfaces 10, 11 against one another, in order to provide the external locking of said optical unit in said rim.

Advantageously, the protrusion 12 is arranged to, during its mounting in the groove 13 by internal tilting of the optical unit 3, form a hinge for the folding back of the front bearing surface 10 of said optical unit against the rear bearing surface of the rim 2 for the purpose of the external locking of said optical unit.

Furthermore, the outer edges 2e, 3e are arranged to, during this folding back, provide the elastic deformation of one of said outer edges by bearing on the other outer edge 2e, 3e in order to allow for the arrangement of the button 18 in the cavity 19. In particular, the outer edges 2e, 3e are of sufficient length to authorise a slight relative displacement. Then, the button 18 and the cavity 19 coming from a structure made of a rigid material, they make it possible to guarantee the reliability of the locking.

In the embodiments shown, the outer edge 3e of the optical unit 3 has a front geometry which is complementary with the rear geometry of the outer edge 2e of the rim 2. More precisely, the recess 7 of each rim 2 has a lateral extension 21 that extends over the rear geometry of the outer edge 2e, with the front geometry of the outer edge 3e being, in the assembled state, with a front bearing on said extension.

In particular, the cavity 19 and the button 18 are formed respectively in the lateral extension 21 and on the front geometry of the outer edge 3e, in particular by each being on their free end. Moreover, the button 18 and/or the cavity 19 can be arranged so that the arrangement of said button in said cavity is accompanied by a characteristic clipping noise, in order to indicate to the wearer that the locking of the optical unit 3 in the rim 2 has been carried out correctly.

As such, the optical unit 3 is mounted in a stable and reliable manner in the rim 2, in particular by limiting as much as possible the risks of untimely withdrawal of said optical unit, which can for example occur following the deformation stresses that the frame 1 is subjected to during the use of the goggles.

In order to withdraw an optical unit 3, the wearer must first externally unlock the optical unit 3 by withdrawing the button 18 from the cavity 19, for example by manually pressing on said button and/or by deforming one of the outer edges 2e, 3e. In order to carry out this unlocking, the wearer can exert a manual force towards the front on the outer edge 2e, in particular by means of his index finger in the vicinity of the free end of said outer edge, combined with an effort towards the rear on the button 18, in particular by pressing by means of his thumb.

Then, the wearer has to withdraw the protrusion 12 from the groove 13 in order to totally withdraw the optical unit 3 from the rim 2. To do this, the wearer can tilt towards the rear the outer edge 3e of the optical unit 3, and this by using the hinge formed by the protrusion 12 which is still arranged in the groove 13, so as to separate said outer edge from the outer edge 2e of the rim 2. Finally, the wearer only has to carry out a simple movement of traction outwards in order to withdraw the protrusion 12 from the groove 13.

In relation with FIGS. 1 to 3, a first embodiment is described hereinbelow, in particular for goggles intended for the practice of an aquatic activity such as swimming.

In particular, the outer edge 3e and the front bearing surface 10 of each optical unit 3 are formed directly on the transparent wall 5, and the assembling of the optical unit 3 in a rim 2 is arranged to provide in particular the seal of the press between the bearing surfaces 10, 11, in order to prevent water from penetrating inside the optical unit 3.

Moreover, the transparent wall 5 of each optical unit 3 has a rear periphery that is provided with a seal 6 intended to hug the face of the wearer, in particular in order to prevent water from penetrating between his eye and said transparent wall. In particular, the seal 6 can be made from a flexible elastomer material and be arranged to provide a sealed peripheral bearing around the eye of the wearer.

Each outer edge 2e, 3e further has a tab 16, 17 that extends towards the rear from its free end, said tab supporting respectively the button 18 and the cavity 19.

In particular, the tab 16 of each rim 2 extends towards the rear from the complementary bearing surface 11 and comprises a free end provided with a slot 20 in order to allow for the attachment of a device for maintaining goggles on the head of the wearer, for example an elastic band of adjustable length. In particular, the slot 20 can allow for the insertion directly of an attaching strap or, as shown, via a part intended to be fastened in the slot 20.

Likewise, the tab 17 of each optical unit 3 extends towards the rear from the outer edge 3e of the transparent wall 5 by laterally exceeding the seal 6.

Figure 1B:
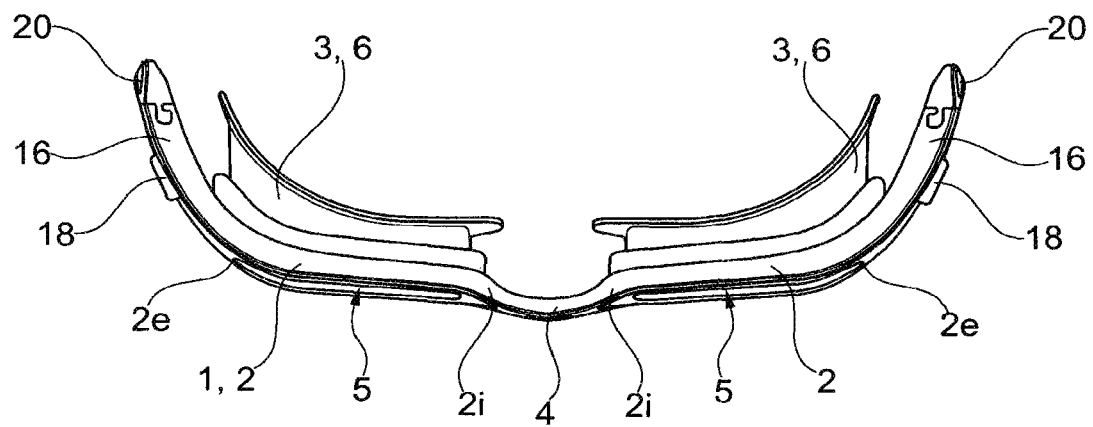
FIG. 1b partially shows goggles according to a first embodiment of the invention, as a bottom view.
Figure 1C:
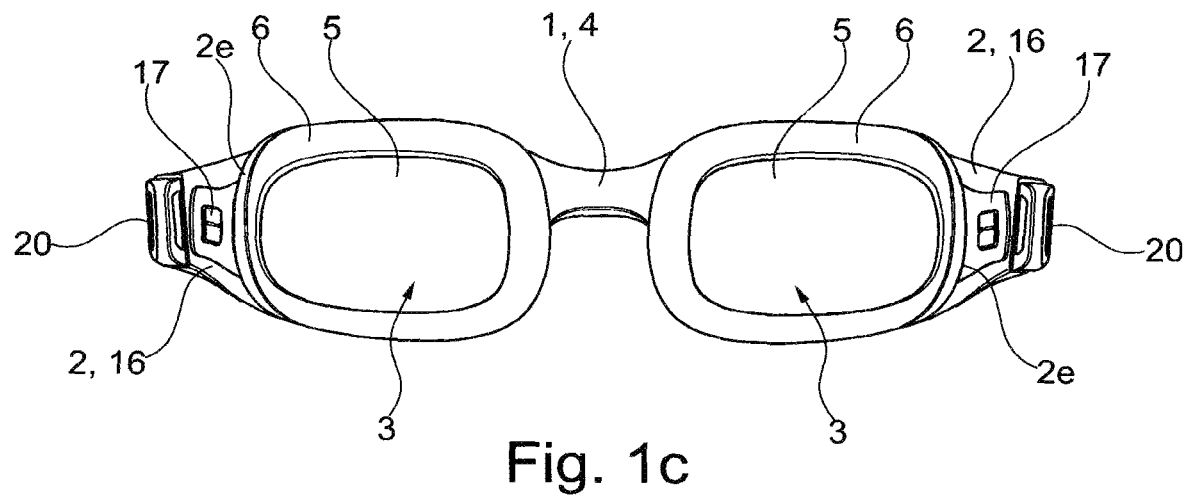
FIG. 1c partially show goggles according to a first embodiment of the invention, as a rear view.
Figure 2C:
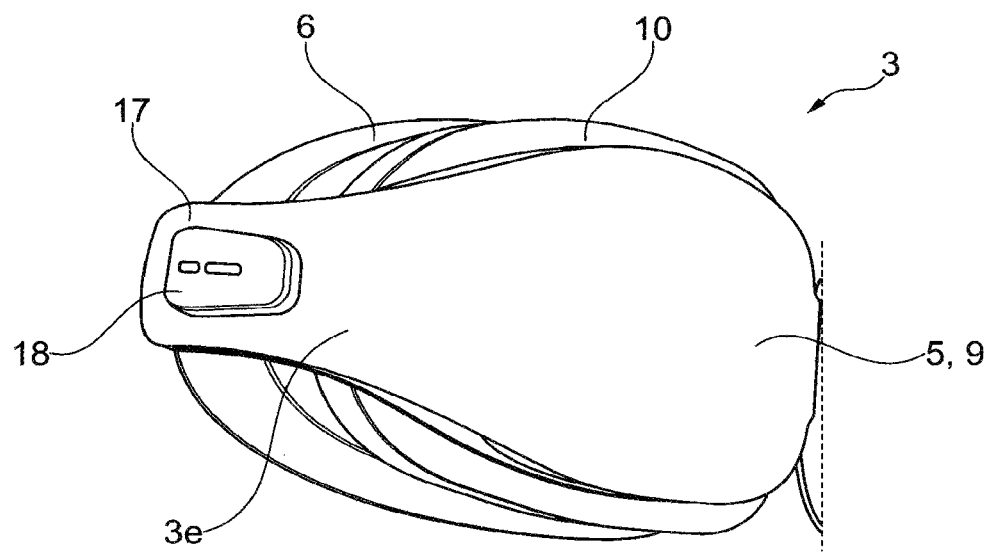
FIG. 2c partially shows an optical unit of the goggles according to FIGS. 1a to 1c, as an outer side view.
Figure 3B:
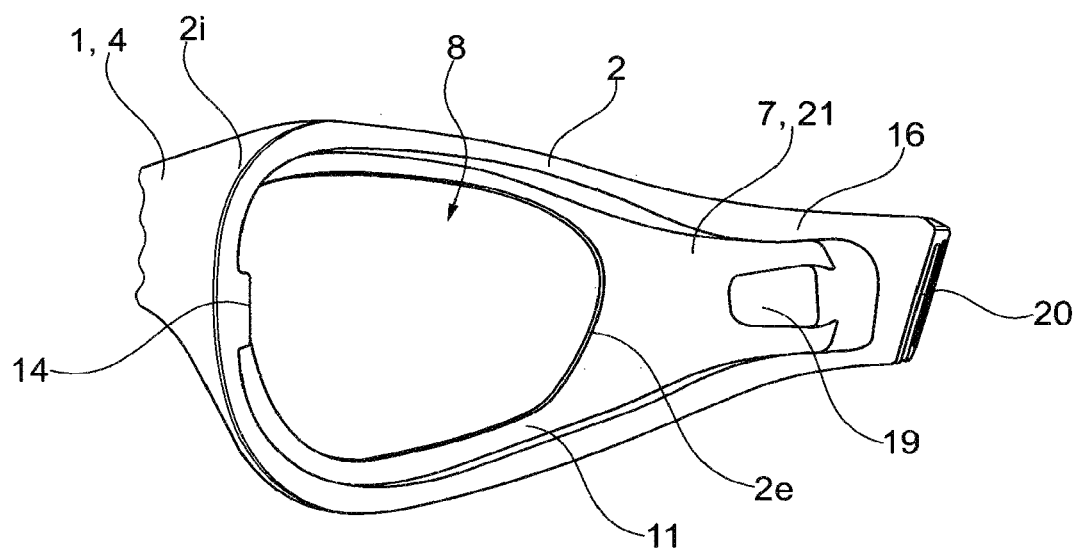
FIG. 3b partially shows a rim of the goggles according to FIGS. 1a to 1c, as a rear view oriented outwards.

In FIGS. 1 to 3, the cavity 19 is formed laterally in the tab 16 of the rim 2, in particular by opening laterally from said tab. Moreover, the button 18 extends exteriorly from the tab 17 of the optical unit 3 and is arranged in such a way as to be able to be withdrawn from the cavity 19 by a lateral manual press thereon.

Advantageously, the outer surface of the tab 16 can be covered with a flexible elastomer material that covers at least the cavity 19, masking the button 18 when it is arranged in said cavity while still allowing it to be actuated manually, which makes it possible in particular to provide the seal by preventing any infiltration of water on said cavity.

Moreover, at least one of the tabs 16, 17 can be reversibly deformable to allow the placement and the withdrawal of the button 18 in the cavity 19 when the bearing surfaces 10, 11 are arranged against one another.

As such, the tabs 16, 17 can be arranged to, during the folding back of the front bearing surface 10 of the optical unit 3 against the rear bearing surface 11 of the rim 2, provide the elastic deformation of one of said tabs by pressing on the other tab 16, 17, in order to allow for the arrangement of the button 18 in the cavity 9. In particular, the tabs 16, 17 are of sufficient length to authorise a slight relative displacement.

Furthermore, in order to withdraw the button 18 from the cavity 19, the wearer can manually press on said button and/or deform one of the tabs 16, 17, for example by exerting with his index finger a manual force towards the front on the free end of the tab 16, combined with a pressing on the button 18 with his thumb.

In relation with FIG. 4, a second embodiment is described hereinbelow, in particular for eyeglasses and/or sunglasses. In particular, each outer edge 2e of the rim has an extension 20a that extends towards the rear from its free end and which is arranged to allow for the mounting in rotation of a foldable branch in order to provide the maintaining of the goggles on the head of the wearer.

Each optical unit 3 comprises a glass 22 wherein is formed the transparent wall 5 and of which the periphery is provided with an adapter 23. In particular, the adapter 23 is made from polymeric material by surrounding the periphery of the glass 22, said adapter being able to be associated irreversibly, for example by overmoulding.

Alternatively, the association can be reversible, for example by providing that an adapter can allow for the mounting of several types of glass 22, which differ by their function and/or by their thickness.

In particular, the adapter 23 and the glass 22 have complementary geometrical means of association. In relation with FIG. 4c, each glass 22 and each adapter 23 respectively have a groove 28 and a complementary association rib 29 that extend respectively along the outer periphery of the glass 22 and along the inner periphery of the adapter 23. Alternatively, the periphery of the glass 22 can be provided with the rib, with the periphery of the adapter 23 then having the groove.

The outer edge 3e and the front bearing surface 10 are formed on the adapter 23 which can be optimised more easily than the glass 22 in order to guarantee the function of assembly of the optical unit 3 in the rim 2. In particular, the outer periphery of the adapter 23 has a step 24 whereon is formed the front bearing surface 10, said step pressing on the rear bearing surface 11, said bearing surfaces being able to extend over all or a portion of the peripheries respectively of the adapter 23 and of the rim 2.

The invention claimed is:

1. A pair of goggles comprising a frame provided with a device for maintaining said goggles on the head of a wearer, said frame having two rims in which an optical unit is respectively intended for being assembled via a reversible attachment device, with each one of said devices comprising complementary geometrical means provided on an inner edge of respectively the rim and the optical unit, said means comprising a protrusion and a groove wherein said protrusion is able to be mounted in order to provide an inner attachment of said optical unit in said rim, with each one of said reversible attachment devices comprising a button rigidly connected to an outer edge of one among the optical unit and the rim and a cavity formed in an outer edge of the other among the optical unit and the rim, said button being capable of being inserted into said cavity in order to provide external locking of the optical unit in the rim, each rim having a recess opening onto a rear, each optical unit having a front bearing which, in an assembled state, is arranged against a rear complementary bearing surface of said recess, at least one of the outer edges being reversibly deformable to allow the placement and the withdrawal of said button in said cavity when the bearing surfaces are arranged against one another.

2. The pair of goggles according to claim 1, and least one outer edge is provided with a tab extending towards the rear, said tab supporting the button or the cavity.

3. The pair of goggles according to claim 1, and the complementary geometrical means are arranged so that the protrusion can first be mounted in the groove, with the later displacement of the bearing surfaces against one another allowing for the external locking of said mounting by arrangement of the button in the cavity.

4. The pair of goggles according to claim 3, and the protrusion is arranged to be mounted in the groove by an internal tilting of the optical unit, the protrusion mounted in the groove thus forming a hinge for allowing a folding back of the front bearing surface of said optical unit against the rear bearing surface of the rim for the purpose of the external locking of said optical unit.

5. The pair of goggles according to claim 4, and the outer edges are arranged to, during the folding back, provide for the elastic deformation of one of said edges by pressing on the other of said edges in order to allow for the arrangement of the button in the cavity.

6. The pair of goggles according to claim 1, and the groove is formed between the complementary bearing surface and a rear protrusion formed inside the rim.

7. The pair of goggles according to claim 1, and the outer edge of a rim extends laterally from the complementary bearing surface.

8. The pair of goggles according to claim 1, and a recess has a lateral extension that extends over a rear geometry of the outer edge of the rim, with a front geometry of the outer edge of the optical unit, in the assembled state, pressing on the front on said extension.

9. The pair of goggles according to claim 8, and the cavity is formed in the lateral extension of the recess (7), the button extending over the front of the outer edge of the optical unit.

10. The pair of goggles according to claim 1, and the cavity is formed in the outer edge of the rim, the button extending over a front of the outer edge of the optical unit.

11. The pair of goggles according to claim 1, and the button can be withdrawn from the cavity by manual pressing thereon.

12. The pair of goggles according to claim 1, and the outer edge of a rim comprises a free end provided with a means of attaching the device for maintaining said goggles on the head of the wearer.

13. The pair of goggles according to claim 1, and the frame comprises a nose bridge that connects the inner edges of each one of the rims.

14. The pair of goggles according to claim 1, and each optical unit comprises a transparent wall of which a rear periphery is provided with a seal intended to hug a face of the wearer, with the outer edge and a front bearing surface being formed on said transparent wall.

15. The pair of goggles according to claim 1, and each optical unit comprises a glass of which a periphery is provided with an adapter, with the outer edge and a front bearing surface being formed on said adapter.

16. The pair of goggles according to claim 15, and the adapter and the glass have complementary geometrical means of association.

* * * * *